United States Patent
Noar (10) Patent No.: US 12,138,057 B2
(45) Date of Patent: Nov. 12, 2024

(54) METHOD AND SYSTEM FOR MONITORING INTERNAL BODILY DISORDERS BY DETECTING AND ANALYZING TISSUE FREQUENCIES

(71) Applicant: Mark D. Noar, Owings Mills, MD (US)

(72) Inventor: Mark D. Noar, Owings Mills, MD (US)

(73) Assignee: ENDOSURE, INC., Sparks Glencoe, MD (US)

( * ) Notice: Subject to any disclaimer, the term of this patent is extended or adjusted under 35 U.S.C. 154(b) by 407 days.

(21) Appl. No.: 17/667,695

(22) Filed: Feb. 9, 2022

(65) Prior Publication Data

US 2022/0386921 A1 Dec. 8, 2022

Related U.S. Application Data (63) Continuation-in-part of application No. 17/338,876, filed on Jun. 4, 2021, now Pat. No. 11,806,161.

(51) Int. Cl.
*A61B 5/265* (2021.01)
*A61B 5/00* (2006.01)
(Continued)

(52) U.S. Cl.
CPC ............ *A61B 5/265* (2021.01); *A61B 5/0022* (2013.01); *A61B 5/0028* (2013.01); *A61B 5/256* (2021.01); *G16H 40/60* (2018.01); *G16H 50/20* (2018.01)

(58) Field of Classification Search
CPC ..... A61B 5/265; A61B 5/0022; A61B 5/0028; A61B 5/256; A61B 5/72–5/7296;
(Continued)

(56) References Cited

U.S. PATENT DOCUMENTS

| | | | |
|---|---|---|---|
| 7,160,254 B2 * | 1/2007 | Noar ...................... | A61B 5/392 600/529 |
| 8,712,515 B2 * | 4/2014 | Faupel .................... | A61B 5/24 600/407 |

(Continued)

FOREIGN PATENT DOCUMENTS

WO 2019143790 A1 7/2019

OTHER PUBLICATIONS

International Search Report & Written Opinion in PCT/US2023/12375 dated May 1, 2023.

(Continued)

*Primary Examiner* — Jonathan T Kuo
(74) *Attorney, Agent, or Firm* — Manelli Selter PLLC; Edward Stemberger (57) ABSTRACT

A method of determining and treating disordered tissue in a patient incites energy signal generation from disordered tissue. An energy sensor structure obtains an energy signal from tissue of a patient. The obtained energy signal is compared in a processor circuit to a known energy signal of the same tissue under normal functioning of the tissue. The tissue is identified as disordered tissue when the comparing step determines that the obtained energy signal is different from the known energy signal. The disordered tissue is localized within the patient via the energy signal. A bodily disorder caused by the localized disordered tissue is diagnosed by an AI module. The bodily disorder is then treated.

21 Claims, 8 Drawing Sheets

(51) Int. Cl.
*A61B 5/256* (2021.01)
*G16H 40/60* (2018.01)
*G16H 50/20* (2018.01)

(58) Field of Classification Search
CPC ........ G16H 40/60; G16H 50/20; G16H 20/40; G16H 50/00–50/80
See application file for complete search history.

(56) References Cited

U.S. PATENT DOCUMENTS

| | | | |
|---|---|---|---|
| 9,474,482 B2 | 10/2016 | Devanaboyina | |
| 9,943,264 B2 | 4/2018 | Axelrod et al. | |
| 10,499,829 B2 | 12/2019 | Axelrod et al. | |
| 10,512,414 B2* | 12/2019 | Axelrod | A61B 5/397 |
| 11,369,310 B2* | 6/2022 | Noar | A61B 5/392 |
| 11,826,170 B2* | 11/2023 | Navalgund | A61B 5/0004 |
| 2005/0215917 A1* | 9/2005 | Noar | A61B 5/392 600/546 |
| 2010/0049078 A1* | 2/2010 | Faupel | A61B 5/24 600/547 |
| 2014/0243814 A1* | 8/2014 | Noar | A61B 18/02 607/40 |
| 2015/0248833 A1 | 9/2015 | Arne et al. | |
| 2017/0055871 A1* | 3/2017 | Axelrod | A61B 5/296 |
| 2017/0332961 A1* | 11/2017 | Noar | A61B 5/7225 |
| 2018/0256092 A1* | 9/2018 | Obma | A61B 5/4887 |
| 2018/0317800 A1 | 11/2018 | Coleman et al. | |
| 2019/0350483 A1 | 11/2019 | Noar | |
| 2019/0350484 A1 | 11/2019 | Coleman et al. | |
| 2020/0107781 A1* | 4/2020 | Navalgund | A61B 5/0004 |
| 2021/0244941 A1* | 8/2021 | Daniels | A61N 1/36003 |

OTHER PUBLICATIONS

Spitzer, Justin, Medical Wearables: Designing for Daily Life, 2021, obtained from worldwide web at HTTPS: experience.molex.com/medical-wearables-designing-for-daily-life/ on May 26, 2021.

* cited by examiner

METHOD AND SYSTEM FOR MONITORING INTERNAL BODILY DISORDERS BY DETECTING AND ANALYZING TISSUE FREQUENCIES

This application is a continuation-in-part of U.S. patent application Ser. No. 17/338,876, filed on Jun. 4, 2021.

FIELD

The invention relates to a system and method for monitoring internal bodily disorders by detecting and analyzing tissue frequencies and thus, provide information for treatment of the bodily disorder.

BACKGROUND

Many bodily diseases present only in their most severe forms at which time symptoms are present. For example, many internal bodily disorders such as, endometriosis, bowel obstruction, possible tumors, etc., require the use of endoscopy or laparoscopy techniques to locate and diagnose the bodily disorder so as to be later treated, for example, by surgery. These techniques are invasive, costly and require the patient to be treated in a hospital setting or at other medical facilities.

Early disease detection is traditionally associated with the ability to often cure and, at the very least, limit the advancement to more serious complications requiring invasive therapy. Being able to diagnose the more subtle forms of the disease carries an obvious advantage.

Accordingly, there is a need to provide a novel method and home-based system to non-invasively identify and determine a specific location and progression of an internal body disorder by monitoring specific frequencies that result from disordered tissue, to analyze frequency data and to transmit the analyzed data for use in treating the bodily disorder.

SUMMARY

An object of the invention is to fulfill the need referred to above. In accordance with the principles of a present embodiment, this objective is obtained by a method of determining and treating disordered tissue in a patient incites energy signal generation from disordered tissue. Energy detecting sensor structure obtains an energy signal from tissue of a patient. The obtained energy signal is compared in a processor circuit to a known energy signal of the same tissue under normal functioning of the tissue. The tissue is identified as disordered tissue when the comparing step determines that the obtained energy signal is different from the known energy signal. The disordered tissue is localized within the patient via the energy signal. A bodily disorder caused by the localized disordered tissue is diagnosed by an Artificial Intelligence (AI) module. The bodily disorder is then treated.

Other objects, features and characteristics of the present invention, as well as the methods of operation and the functions of the related elements of the structure, the combination of parts and economics of manufacture will become more apparent upon consideration of the following detailed description and appended claims with reference to the accompanying drawings, all of which form a part of this specification.

BRIEF DESCRIPTION OF THE DRAWINGS

The invention will be better understood from the following detailed description of the preferred embodiments thereof, taken in conjunction with the accompanying drawings, wherein like reference numerals refer to like parts, in which.

DETAILED DESCRIPTION OF THE EXEMPLARY EMBODIMENTS

Figure 1:
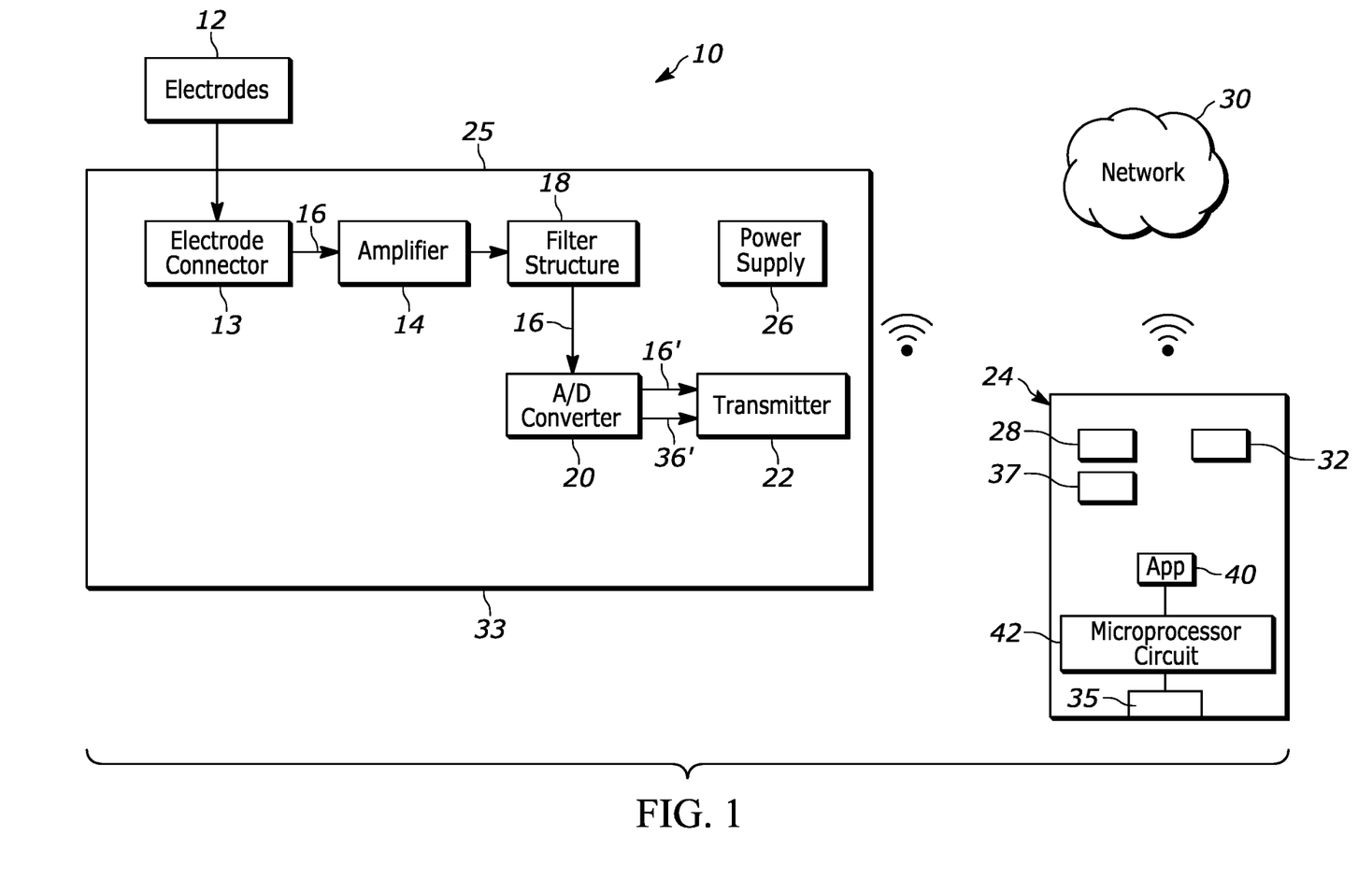
FIG. 1 is a block diagram of a disordered tissue monitoring system provided in accordance with a first embodiment of the invention.

With reference to FIG. 1, an embodiment of a disordered tissue monitoring system for monitoring and diagnosing internal bodily disorders is shown, generally indicated at 10. The system 10 includes energy detecting sensor structure, preferably in the form of electrode structure comprising at least two (preferably three) electrodes 12, each preferably a silver-silver chloride electrode connected, via an electrode connector 13, with an instrumentation amplifier 14 that provides the first gain stage for the electrode electrical signals 16. Filter structure 18 provides a high pass and low pass filtering of the signal 16. The filter structure 18 can include analog (hardware) or digital (software) high-pass and low-pass filters, or a combination of analog and digital filters. The amplifier 14 and filter structure 18 can be combined into a signal conditioner.

The electrical signals 16 are also passed to a 16-bit A/D converter 20. The digitized electrode electrical signals 16' including frequency signals and intensity of the frequency signals are then passed to a transmitter 22, which transfers data (e.g., signals 16') to an external portable handheld device 24 (such as a conventional smart phone, tablet, laptop) or to a network 30 in a wireless manner. When transmitted to the portable device 24, the data is received by a receiver 28 of the portable device 24. In the embodiment, the electrodes 12 are provided outside of a portable unit 25 that can be considered to be a substrate or housing. A power supply 26, such as a battery, powers the unit 25.

The portable device 24 can be considered a processing device that can also communicate in a wireless manner with the network 30 via a transmitter 32 of the portable device 24. The network 30 may include at least one of a telecommunication network such as a computer network (e.g., a LAN or a WAN), the Internet, cloud-based server, and a telephone network.

The portable device 24 can include an application (APP) 40 executed by microprocessor circuit 42 that can analyze the raw data (e.g., signals 16 including at least frequency and intensity of the frequency data) received from the transmitter 22 and provide treatment data including an identification, severity, location and progression of a bodily disorder of a patient based on the raw data. The treatment data can be stored on the network 30, shared or retrieved via the network 30, or can be stored in a memory circuit 35 of the portable device 24. Also, the portable device 24 can receive data from the network 30 via receiver 28.

The transmitter 22 can be in the form of a transceiver so as to also receive data from the portable device 24. For example, the portable device 24 may send a calibration signal 37 to the transceiver 22 that can be received by the amplifier 14 for calibration purposes and determine if the system 10 is performing within specification.

Figure 2:
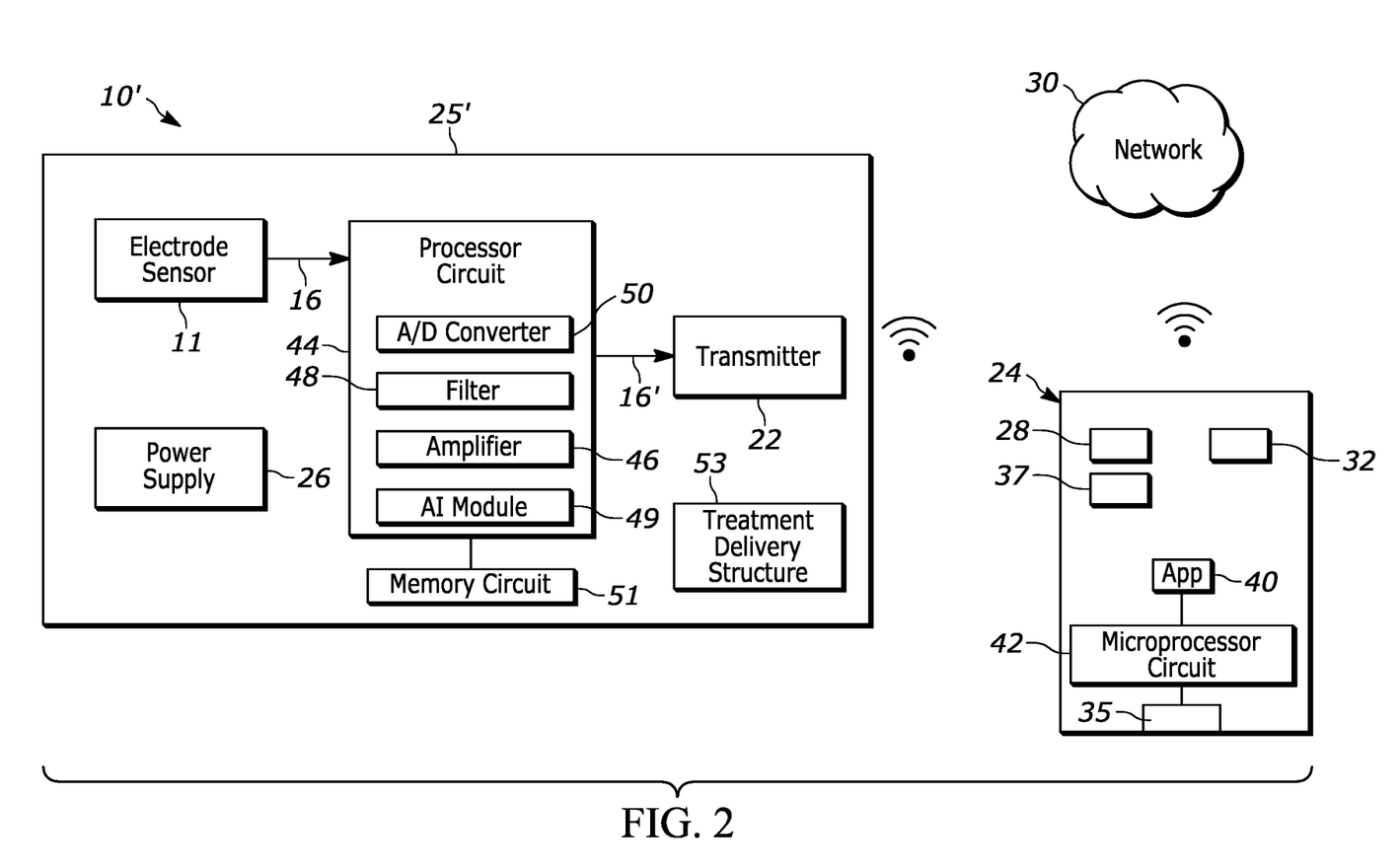
FIG. 2 is a block diagram of a disordered tissue monitoring system provided in accordance with a second embodiment of the invention.

With reference to FIG. 2, a second embodiment of the monitoring system for diagnosing internal bodily disorders is shown, generally indicated at 10'. The system 10' includes an energy detecting sensor structure in the form of a single sensor structure 11 (which can include at least two or a plurality of miniaturized electrodes), disposed within the portable unit 25' and connected with microprocessor circuit 44. The microprocessor circuit 44 is provided in the unit 25' and is constructed and arranged to convert the analog electrical signal 16 to a digitized electrical signal 16' including frequency signals and intensity of the frequency signals. In the embodiment, the microprocessor circuit 44 can include an amplifier circuit 46 constructed and arranged to amplify the analog electrical signals 16, a filter circuit 48 constructed and arranged to filter the amplified analog electrical signals, and an A/D converter circuit 50 constructed and arranged to convert the amplified and filtered analog electrical signals to the digitized electrical signals 16'. The filter structure 48 preferably includes digital high-pass and low-pass filters since digital filters can be made much more accurate than their analog counterparts and are not subject to the same effects of analog component tolerances that lead to less than ideal performance from device to device and over time. Analog components can be manually sorted such that only ideal components are used, but there is considerable cost involved that will drive up the end price to the physician and these components are still subject to the ravages of environmental stresses and time that impairs their accuracy. The microprocessor circuit 44 includes an Artificial Intelligence (AI) module 49 that is configured to execute at least one algorithm to 42 that can analyze the raw data (e.g., signals 16' including at least frequency and intensity of the frequency data) and provide treatment data including an identification, severity, location and/or propagation of a bodily disorder of a patient based on the raw data. Localization and propagation data can be obtained with the AI module 49 by employing conventional triangulation and/or trilateration techniques based on the frequency and intensity data obtained by the energy directing sensor structure (e.g., at least two electrodes) as descried further below. Alternatively, the AI module 49 can be part of APP 40 in the device 24.

The AI module 49 is preferably configured to provide a diagnosis of the suspected bodily disorder due to the disordered tissue. An initial (first level) software analysis performed by the AI module 49 using the 100% sensitivity marker equation. Using the 100% sensitivity marker equation, if the patient tests negative for having bodily disorder (e.g., endometriosis, as explained below), then the patient is no longer considered as having the bodily disorder. If the patient passes the first level analysis, then the programming in the AI module 49 moves to the next memory level (second level) which is to look at a different equations to be certain there is not a false negative. If a false negative is not determined, the patient is considered to have the bodily disorder (e.g., endometriosis).

The AI module incudes a third level that is a much more sophisticated level in which the software is empowered to find answers they were not determined by the first and second level algorithms. The memory circuit 51 includes additional databases of information (e.g., patient's age, symptoms) that the software will be able to access. Such information can include any information that plays a role in diagnostics or at least in the predictability of the bodily disorder. The information that is believed to be of a higher statistical level for predictability should be looked at in this third level program. Thus, in this third level analysis, the AI module is configured to search the information in the memory circuit 51 to bring in the greatest number of variables (information) that results in the highest probability level of a positive diagnosis of the bodily disorder.

It is noted that there are other methods for predicting the presence of a suspected condition. One of these methods is the use of patient questionnaires. The AI module 49 can be configured to have a fourth level analysis (self-aware AI). Programing in the AI module 49 can be configured to be able to ask additional questions to help to confirm the diagnosis. For example, the AI module 49 can query the patient (e.g., via the APP 40) using an extensive, but subjective questionnaires. Thus, the programming in the AI module 49 can decide to include the probabilities of known questionnaire responses to achieve maximal predictability of the bodily condition. Since the system can be a wearable device (see FIG. 7) that interfaces with servers in the network 30, worldwide data can be collected from millions of patients on a daily basis. The AI module 49 can access and analyze the worldwide data and programming in the AI module 409 is configured to "free think" the most important parameters and develop its own internal algorithms, to be able to evolve its own hierarchy in order to maximize diagnostics.

A transmitter 22 is provided in the unit 25' and is constructed and arranged to transmit to the portable device 24 and/or network 30, in a wireless manner, the treatment data noted above. A power supply 26 is provided for powering the device 10'.

Gain in the preferred embodiments of the system 10, 10' is fixed and set according to the greatest peak to peak signal 16 normally expected. The 16 bit A/D converter 20, 50 provides sufficient resolution to adequately process lower level signals, such as may be recorded from a person with substantial amount of fat tissue interposed between the electrodes 12 if placed in direct contact on the skin surface, the stomach or other fatty tissue. Of course, gain may be made controllable either via an analog control or via digital control at additional cost.

Use of the wireless transmitter 22 for data communication with the portable device 24 and/or network or computer 30 removes the need for cumbersome cables and complicated interfaces that each present distinct possibilities for intermittent or total failure that can degrade system performance. The treatment data obtained can be sent wirelessly to the network 30 or portable device 24 via, for example, a cellular signal, Bluetooth® or WIFI. The memory circuit 35 or 51 each provides enough on-board memory to store an entire exam's worth of data for later transmission to the network 30.

Applicant has determined that when an internal bodily disorder is present in the body, the nerves of the tissue causing the disorder exude a specific energy (e.g., frequency) and defines a "fingerprint" of the specific tissue disorder, as compared to normal such tissue. Normal function of tissues and processes in the human body are associated with organs. Specialized tissue and cells that act as controllers are governors of what is known as internal control or homeostasis. Detection of normal tissue frequencies which represent normal homeostasis is valuable in determining the difference between health and disease. When disease occurs, it causes a disorder of the normal controllers or homeostasis and this is then seen as a change in energy or patterns of energy and is representative of underlying disease and symptoms. Thus, the disordered tissue can be non-normal tissue or diseased tissue.

For example, endometriosis is the condition where tissue escapes the uterus causing nervous system issues and pain. The Applicant has determined that when sensing for endometriosis, endometriosis tissue is not sensed directly. However, the effect that the endometriosis tissue has on the energy of the body can be sensed. Endometriosis tissue secretes neurotransmitters which increase the frequency of contraction of the small bowel. Normal conditions of the uterus exude energy at the frequency range of 1-3 cpm, except during menstruation, when the frequency range is 4-8 cpm. The energy effects of the escaped (disordered or non-normal) tissue has been identified as detectable at a frequency range of 12-60 cpm (cycles-per-minute) and, more particularly, near the proximal duodenum at a frequency range of 12-22 cpm, and near the distal duodenum at a frequency range of 30-60 cpm.

As another example, a normal condition of the bowel exudes energy at a frequency range of 3-15 cpm, depending on location in bowel. A bowel spasm or obstruction due to scar tissue (disordered or non-normal tissue) has been identified as detectable near the distal Ileum at a frequency range of 180-200 cpm and near the small bowel at a frequency range of 50-70 cpm. In a further example, urethral disorders can be detected. A normal frequency of urethral tissue to pass urine is 7 cpm. Applicant has been determined that frequencies of at least 18 cpm and above indicates disordered or non-normal urethral tissue. Thus, the energy detecting sensor structure Thus, the filter structure 18, 48 of the systems 10 and 10', respectively, can be configured to detect a frequency range that is known to define the "fingerprint" of any bodily disorder.

To detect endometriosis, the filter structure 18, 48 is selected to have high pass and low pass filters to permit detection of frequencies in the range of 12 to 60 cpm. To detect a bowel obstruction, filter structure 18, 48 is selected to have high pass and low pass filters to permit detection of frequencies in the range of 180 to 200 cpm or in the range of 50 to 70 cpm, depending on where detection is aimed. To detect urethral disorders, the filter structure 18, 48 is selected to have high pass and low pass filters to permit detection of frequencies in the range of 15 to 25 cpm. These filters are generally both of second order, but higher order digital filters can be implemented. An optional second digital filter may be implemented in the software (computer readable medium) for high pass and/or low pass functions to achieve the desired bandpass filtering of the signals 16' prior to software analysis. This approach also provides greater flexibility in the system for changing specific frequency ranges in the digital filter to focus on specific bodily disorders.

Since the system 10, 10' can be employed to locate any internal bodily tissue disorder causing an energy "fingerprint", is preferable that the electrodes 12 or sensor structure 11 be: 1) able to sense a wide area of a bodily portion, 2) either movable relative to each other and to the patient's tissue which they are to be in contact or in proximity with or 3) fixed on a grid, with the grid being movable relative to the patient's tissue which they are to be in contact or in proximity with.

Figure 3:
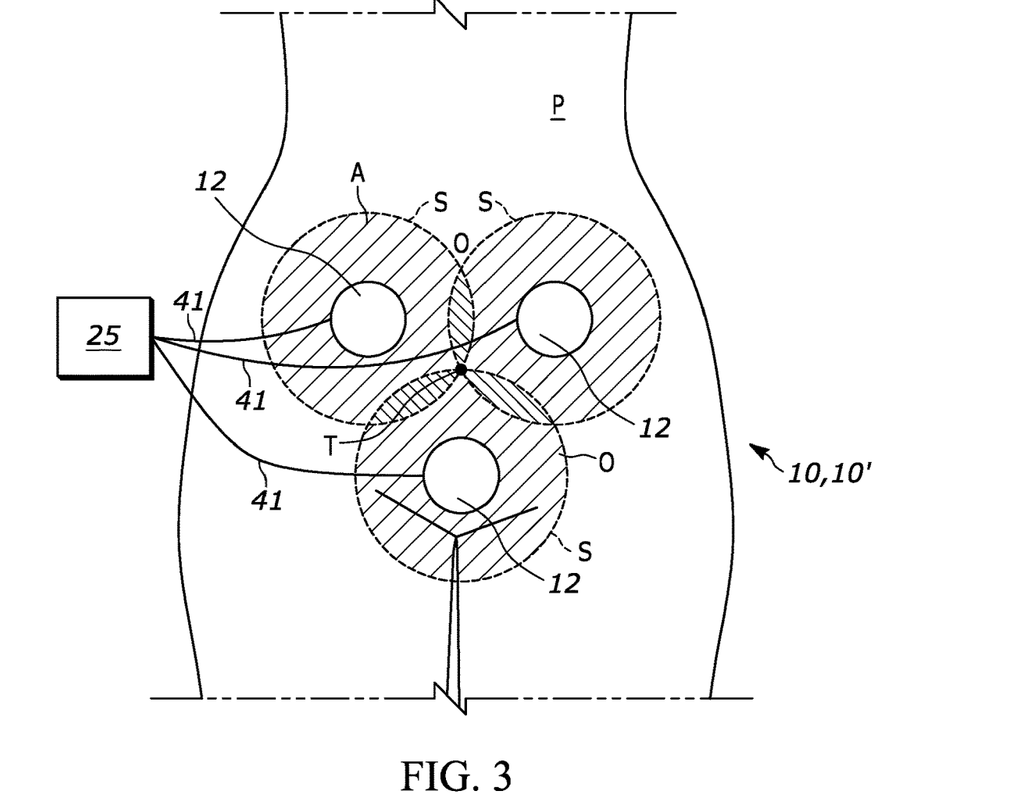
FIG. 3 is a view an embodiment of the system with electrodes thereof mounted on an abdomen of a patient.

With reference to FIG. 3, the system 10, 10' is shown employing the energy detecting sensor structure in the form of a plurality of electrodes 12 (preferably at least three) mounted in contact with or in proximity to a body surface of a patient P. Each electrode 12 has a sensing area S to define an overall sensing area (cross-hatched at A). Sensing areas S overlap at double cross-hatched area O so that the AI module 49 of the microprocessor circuit 42 or 44 can employ triangulation and/or trilateration of the electrode signals upon obtaining the strongest frequency signal (signal intensity) to determine, severity, location and/or propagation (movement or change) of the disordered tissue in three dimensions from at least two, but preferably at least three electrodes 12. If the electrodes 12 are external to the unit 25, electrical connection 41 of each electrode 12 can be connected with the electrode connector 13 (FIG. 1) of the unit 25. The electrodes 12 are preferably disposable. Although multiple overlapping fields of detection are disclosed, it can be appreciated that instead of the plurality of electrodes, a single sensor structure or electrode with a wide sensing field can be provided and placed on or in proximity to the body surface. Still further, such a single, wide sensing field sensor or electrode can be implanted under the skin.

Figure 4:
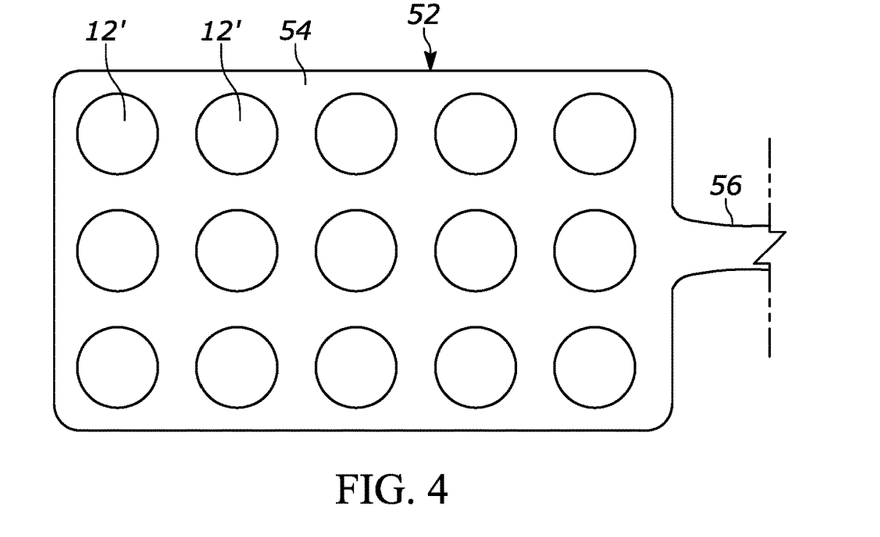
FIG. 4 is a plan view of an electrode grid for use in the system of FIG. 1.

In another embodiment and with reference to FIG. 4, the energy detecting sensor structure is in the form of an electrode array structure, generally indicated at 52, that includes a plurality of electrodes 12' (preferably at least three electrodes 12'), provided in an array or grid that are fixed on a flexible substrate 54. A single connector 56 can connect with the electrode connector 13 (FIG. 1) of the unit 25. The electrode array structure 52 can be placed on the body of the patient and can be moved to different positions so that AI module 49 of the microprocessor circuit 42 or 44 can employ triangulation and/or trilateration of the electrode signals upon obtaining the strongest frequency signal (signal intensity) to determine, severity, location and propagation (movement or change) of the disordered tissue in three dimensions from at least two, but preferably at least three electrodes 12'. Alternatively, the electrode array structure 52 can be placed in a vest that is placed on the patient so that the electrodes 12' are in close proximity to the patient's skin, with the vest being movable so that the AI module 49 of the microprocessor circuit 42 or 44 can employ triangulation and/or trilateration of the electrode signals upon obtaining the strongest frequency signal (signal intensity) to determine, severity, location and propagation (movement) of the disordered tissue in three dimensions from at least two, but preferably at least three electrodes 12'. The electrode array structure 52 is preferably disposable.

Figure 5:
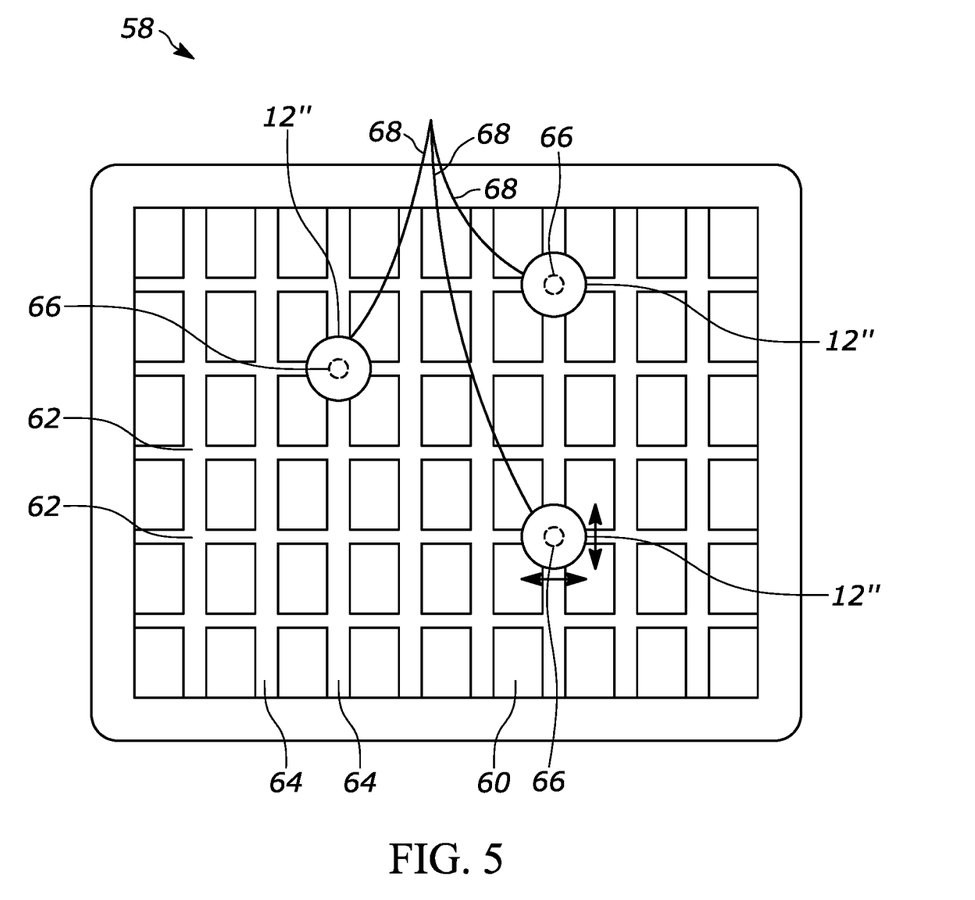
FIG. 5 is a plan view of an electrode slide structure with electrodes movable in slots thereof, for use in the system of FIG. 1.

Alternatively, instead of fixing the electrodes on a flexible substrate, with reference to FIG. 5, an electrode slide structure is shown, generally indicated at 58, that includes a flexible substrate 60 having a plurality of spaced horizontal slots 62 and a plurality of spaced vertical slots 64 therein. A plurality of electrodes 12" (preferably at least three electrodes 12") are provided, each having a base 66 that is frictionally engaged relative to the slots 62, 64 so as to be movable both horizontally and vertically with respect to the substate 60. Electrical connections 68 of the electrodes 12" can be connected with the electrode connector 13 (FIG. 1) of the unit 25. Thus, the electrode slide structure 58 can be placed on the body of the patient and can be moved to different positions on the body and the electrodes 12" can be slid or be moved to different positions on the substrate 60 in order for the AI module 49 of the microprocessor circuit 42 or 44 to employ triangulation and/or trilateration of the electrode signals upon obtaining the strongest frequency signal (signal intensity) to determine, severity, location and propagation (movement or change) of the disordered tissue in three dimensions from at least two, but preferably at least three electrodes 12'. For example, with reference to FIG. 3, when the disordered tissue is partially in more than one of the electrode sensing areas S, using trilateration, the location T of the disordered tissue is at the intersection point of the perimeters of the three electrode areas S. If the three perimeters (circles) do not intersect at a point, then a location area would be obtained. Triangulation can be used when the disordered tissue falls within the sensing area S of only one of the electrodes.

Alternatively, the electrode slide structure 58 can be placed in a vest that is placed on the patient so that the electrodes 12" are in close proximity to the patient's skin, with the vest being movable to different positions on the body and the electrodes 12" can be slid or be moved to different positions on the substrate 60 so that the AI module 49 of the microprocessor circuit 42 or 44 can employ triangulation and/or trilateration of the electrode signals upon obtaining the strongest frequency signal (signal intensity) to determine, severity, location and propagation (movement or change) of the disordered tissue in three dimensions from at least two, but preferably at least three electrodes 12'. The electrode slide structure 58 is preferably disposable.

The energy detecting sensor structure 11, 12, 12', 12" can detect the frequency, frequency intensity, and a direction of origin of the frequency signal of disordered tissue or other tissue that the disordered tissue affects. By using triangulation and/or trilateration as described above, treatment data including severity, localization and propagation of the disordered tissue can be identified. Localization need not be a pinpoint location. Thus, if the frequency of the monitored tissue is within the "fingerprint" range caused by the specific disordered tissue, the treatment data regarding the disordered tissue is obtained. Also, a localization of the disordered tissue and other characteristics such as propagation can be determined by the system 10, 10' so that treatment can be effected without further invasive endoscopy or laparoscopy locating procedures. For example, a bowel obstruction can be detected based on a certain disordered frequency of the bowel tissue or other tissue affected by the disordered bowl tissue as compared to a normal frequency as noted above. If the intensity (strength) of the frequency signal (e.g., caused by contacting of muscle) remains constant over a defined area, this would indicate a static location of blockage. If, however, the intensity of the frequency signal is detected to increase over a distance and then reduce, propagation (change and severity or extent) of the blockage (disordered tissue) is determined. For example, the bodily disorder of endometriosis may change during a woman's menstrual cycle, as may the associated enteric nervous system spasm, or a bowel blockage can change location or involve variable portions of the gastrointestinal system. When the bowel obstruction is fixed or static, the propagation is zero. The amount of time it takes for a frequency signal to move from one location to a second location along the disordered tissue and the distance between the two locations can be obtained by the AI module 49 and used to determine the propagation of the disordered tissue and/or location of the obstruction or disorder. Thus, the system 10, 10" can determine the focal point of the disordered tissue as well as the extent of the disordered tissue, e.g., upstream, downstream or at a location different from the focal point.

It is noted that the units, 25 25' (e.g., the energy detecting sensor structure such as the at least two electrodes, the amplifier, the filter structure, the A/D converter, the microprocessor circuit, and the transmitter) can be miniaturized down to a single integrated circuit with a miniature power source as to portable, flexible wearable and disposable. Thus, the housing may not be required, or a flexible substrate of the integrated circuit can be considered to be the housing. To enhance wearability, miniaturized or not, the units 25, 25' are preferably flexible and sweat or water resistant. For example, with reference FIG. 7, if a general mounting location on the body is known, the integrated circuit 25, 25'could be configured into a medical skin patch 78 or can replace the pad of an adhesive bandage so as to be adhered and worn on the user's skin. The skin patch 78 can have a portion 80 covering over the integrated circuit and can include a mounting portion 82, the underside of which and be adhered to skin. Alternatively, the integrated circuit could be mounted on the body using a self-adhering bandage (e.g., wrapped around the abdomen), or can be incorporated on a belt, so as to be able to be moved to different locations on the body and remounted if needed. Thus, the unit 25, 25', when worn by the patient, can obtain data over a period of time and transmit data over the network 30.

Figure 7:
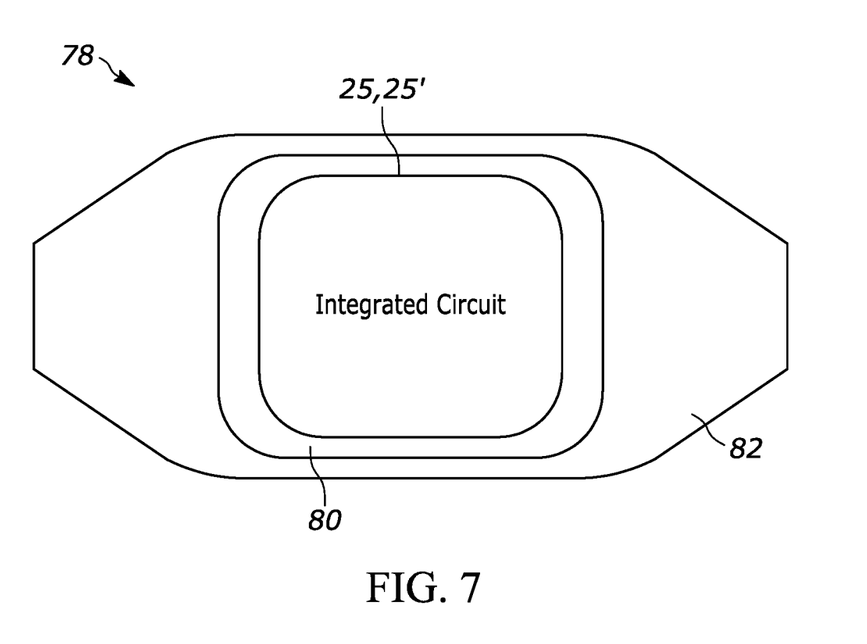
FIG. 7 is a plan view of a medical skin patch incorporating an integrated circuit containing components of the system.

Once the treatment data is obtained by the system 10, 10', the system 10, 10' can notify the user to initiate treatment. Treatment can be performed, for example, by modulating the disordered tissue directly with energy such as electro-magnetic frequency (EMF) or electric stimulation or shock treatment from a treatment delivery structure 53 included in the unit 25' (FIG. 2). The treatment delivery structure 53 can be of the type disclosed in U.S. Patent Application Publication No. 20170332961 A1, the content of which is hereby incorporated by reference herein. The treatment delivery structure 53 can be separate from and outside of the unit 25' (e.g., drugs or hormones) and implanted or disposed on the body of the patient and can communicated wirelessly with the network 30 or portable device 24. The drugs or hormones can be delivered directly to the disordered tissue or to tissue nearby the disordered tissue to treat the bodily disorder associated with the disordered tissue. Thus, treatment of the disordered tissue can be done directly to the disordered tissue or indirectly. The microprocessor circuit 42 or 44 can signal the treatment delivery structure 53 to deliver the treatment. Alternatively, treatment can be removal of the disordered tissue by surgery. If drug or hormone treatment is employed, the treatment delivery structure 53 that is disposed on or implanted in the patient can, instead of delivering EMF or electric stimulation or shock, deliver the drug or hormone to the disordered tissue or tissue nearby on demand as needed to calm the disordered tissue by being controlled by an APP on the portable device 24, preferably upon authorization from a doctor. For example, if the system 10, 10' detected an abnormality in the motility of the gastrointestinal tract, the treatment delivery structure 53 could deliver treatment (drug, EMF, etc.) to speed-up the motility, slow down or even stop the motility. Alternatively, if the unit 25' is in the form of an integrated circuit on a medical skin patch 78, the treatment delivery structure 53 can be the patch itself, so that the drugs or hormones can be delivered trans-dermally via the patch, or the patch 78 can communicate instructions wirelessly to a different skin patch (not shown) that delivers the treatment. The unit 25' can also have input buttons for initiating controls.

The treatment data obtained or received by the portable device 24 or computer 30 can include color-coded data. For example, different frequencies can be assigned different colors such as, the frequency indicative of abnormal tissue can be color-coded as red, while other normal frequencies can be blue in color. The intensity of the frequency signals can also be displayed with the data.

Figure 6:
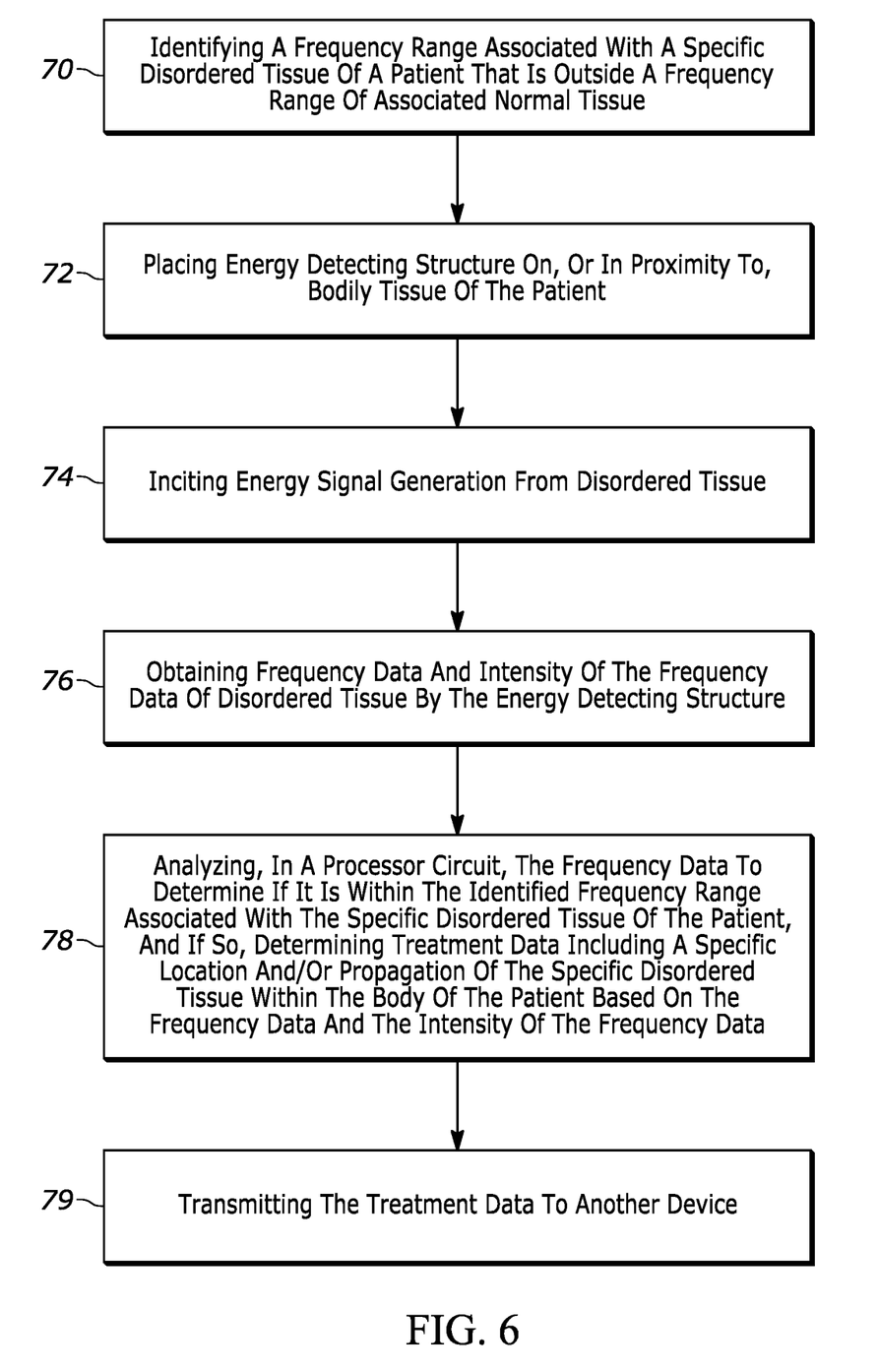
FIG. 6 is a flow chart of steps of a method of an embodiment.

Thus, by employing the algorithms outlined above, with reference to FIG. 6, a method of monitoring disordered tissue in a patient includes in step 70, identifying a frequency range associated with a specific disordered tissue of a patient (e.g., based on the "fingerprint" noted above) that is outside a frequency range of associated normal tissue. In step 72, the energy detecting sensor structure 11, 12, 12', 12" is placed on, or in proximity to bodily tissue of the patient. In step 74, energy signal generation is induced, such as by employing a water load test or any number of other methods that cause stimulation of the disordered tissue, so that the disordered tissue gives off the "abnormal" frequency or energy signal that can be detected. The water load test is conventional and involves the patient consuming an amount of water that enters the stomach. In step 76, frequency data and intensity of the frequency of the disordered tissue is obtained by the energy detecting sensor structure. In step 78, the frequency data is analyzed by the microprocessor 42, 44 to determine if it is within the identified frequency range associated with the specific disordered tissue of the patient, and if so, the AI module 49 of the microprocessor 42, 44 determines, by trilateration, a specific location of the disordered tissue within the body of the patient. In step 79, the frequency data and location data are optionally transmitted to another device. Although, as described above, the transmission of data is preferably in a wireless manner, it is within the contemplation of the embodiment that transmission can include transferring data in a wired manner. The AI module 49 is configured to determine a diagnosis of the bodily condition caused by the disordered tissue, as explained above. Once a patient is known to have the bodily disorder caused by the disordered tissue, treatment can then be performed by, for example, modulating the disordered tissue with EMF, performing surgery, or delivering drugs or hormones to the patient. Thus, personalized treatment that is dependent upon the signal generated can be performed. Therefore the same system 10, 10' that is able to detect the abnormal signal of the disordered tissue is able to direct therapy or treatment either via another, separate device (not shown) or via the same system 10' (see FIG. 2, via the treatment delivery structure 53).

After the therapeutic treatment, the system 10, 10' can be employed again immediately thereafter, after a delayed period, or after a long period of time to determine if there is a change of the sensed frequency at the location(s) where the disordered tissue was previously identified.

Although embodiments for endometriosis and bowel obstructions have been disclosed, the system 10, 10' can be configured to locate any internal bodily disorders by ensuring detecting of the proper frequency range, so long as the disorder exudes an energy "fingerprint" as noted above. For example, but not limited to, the following organs/tissues with associated diseased states can be identified by the system 10, 10' and method herein by identifying a disease state when energy obtained from the suspected diseased organ/tissue is different from the known energy of the organ/tissue at a normal functioning condition:

Ureters, normal condition=1-4 cpm
    Disease states: obstruction, stones, cancer
Urinary Bladder, normal condition=2-4 cpm
    Disease states:
        Cystitis due to infection or autoimmune or other causes
        Bladder spasm
        Cancer, infiltrative disease like autoimmune disease
        Obstruction such as kidney stones
Fallopian Tubes, normal condition=1-4 cpm, except during ovulation then 8-12 cpm
    Frequencies are related to menstrual cycle and can allow prediction of ovulation and optimal time for fertility
    Disease states:
        Obstruction, tubal pregnancy
Uterus, normal condition=1-3 cpm, except during menstruation then 4-8 cpm
    Disease states:
        Adenomyosis, tumor
        Motility disturbances affecting fertility
Biliary system, normal condition=1-2 cpm
    Disease states:
        Stones, strictures, tumors, obstruction
        Abnormal frequencies in the 12-18 cpm range
Large and Small bowel, normal condition=3-15 cpm, depending on location in bowel
    Disease states:
        Inflammatory bowel disease and obstruction or modify the contractility.
        Medication is used to control these diseases but it is not often possible to determine that it works. Sensing the return to normal homeostatic frequency can be used to show return to normal avoiding invasive testing.
Stomach, normal condition=3 cpm
    Disease state: Ulcer
Aorta and other large vessels
    Disease states:
        Aneurysm
        Blockages The system 10, 10' is configured for external use on person under study. However, devices such as the catheter structure as disclosed U.S. Pat. No. 8,753,340, the content of which is hereby incorporated by reference herein, can be modified to sense the effects of disordered tissue internally of the body using the electrodes thereof, and/or can deliver treatment to the internal disordered tissue. Thus, with reference to FIG. 8, another embodiment the system 10''', in the form of a catheter structure, is shown inserted via an endoscope 84 or the like to access tissue in a human organ 86, such as a stomach, uterus, bowel, or other internal organs or human systems noted above The system 10''' includes an elongated tube structure 88 having a distal end 90 and a proximal end 92. Thus, the system 10''' with tube structure 88 can be inserted into any bodily orifice to access and treat disordered tissue. Energy detecting sensor structure, preferably three electrodes 12''', are associated with the distal end 90 of the tube structure 88 so as to preferably be moved from a substantially retracted position with respect to distal end 90 of the tube structure 88 to an operative position extending directly from the distal end 90. A signal wire 94 is associated with each electrode 12''' for obtaining signals from the electrodes as will be explained more fully below. The wires 94 extend within the tube structure 88 to the proximal end 94 thereof.

Figure 8:
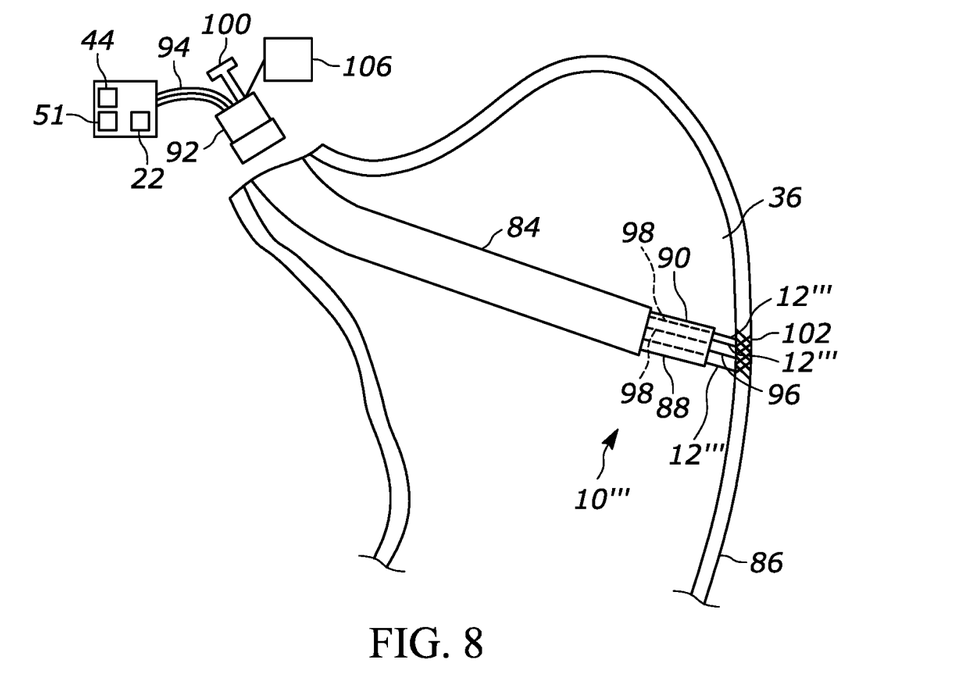
FIG. 8 is perspective view of anther embodiment of the system, provided in accordance with the principles of the invention, shown inserted into a stomach with electrodes and treatment delivery structure thereof engaged with disordered tissue of the stomach.

Treatment delivery structure 96, separate from the electrodes 12''', is also provided in the tube structure 88. When being inserted into the human organ 86, the electrodes 12''' and treatment delivery structure 96 are in an insertion position. More particularly, the electrodes 12''' and treatment delivery structure 96 are retracted, disposed near the distal end 90 and preferably inside of tube structure 88. The electrodes 12''' and treatment delivery structure 96 are delivered via the tube structure 88 that is passed through the biopsy channel of a standard endoscope 84. In the illustrated embodiment, three electrodes 12''' are provided, one for a positive signal, one for a negative signal and one for ground.

Figure 9:
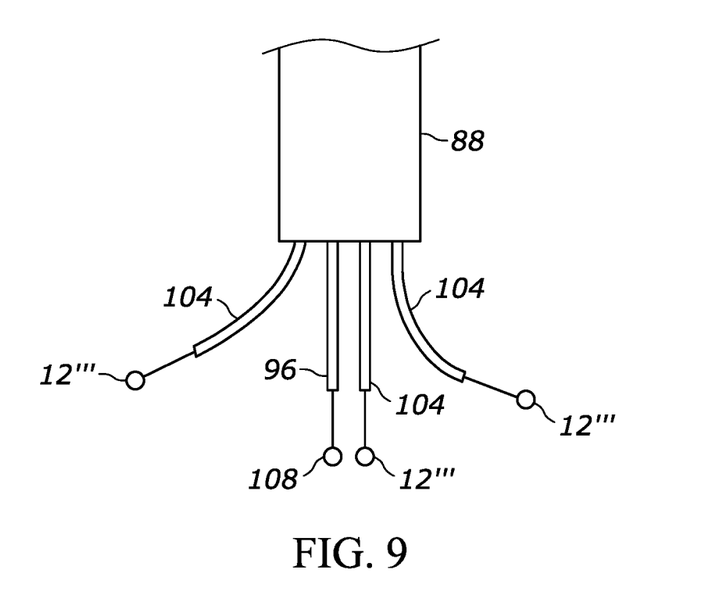
FIG. 9 is an enlarged side view of a distal end of an embodiment relating to the system of FIG. 8.

In one embodiment, to move the electrodes 12''' and the treatment delivery structure 96 between the retracted and extended positions, actuating structure 98, 100 is provided. In the embodiment, the actuating structure can be, for example, one or more wires 98 operatively associated with the electrodes 12''' that are manually movable separately, or in unison at the proximal end of the tube structure 88. For example, FIG. 1 shows a single plunger 100 coupled to the wires 98. Movement of the plunger 100 extends and retracts the electrodes 12''' preferably in unison. Alternately, instead of retracting and relocating the electrodes 12''' to search for the disordered tissue such as an ulcer 102, with reference to FIG. 9, the system 10''' can include a plurality of lumens 104 within the tube structure 88. Each lumen 104 contains a different electrode 12''' so that each electrode 12''' can be directed separately in different directions to expand the diagnostic tracking location and allow multi-treatment and sensing sites. In the embodiment of FIG. 9, the electrodes can be retractable for ease of inserting/removing the system 10' to/from the disordered tissue site.

Returning to FIG. 8, the system 10''' includes the processor circuit 44, memory circuit 51 and transmitter 22 of FIG. 2. Thus, the processor circuit 44 includes the filter 48 with the appropriate signal filtering for sensing of the frequencies associated with the targeted, disordered tissue. The microprocessor circuit 44 includes the Artificial Intelligence (AI) module 49 (FIG. 2) that is configured to execute at least one algorithm that can analyze the raw data (e.g., signals such as frequency and intensity of the frequency data) and provide treatment data including an identification, severity, location and/or propagation of a bodily disorder of a patient based on the raw data, as noted above. For treatment by electrically stimulating tissue, a source of energy 106, preferably electrical energy is provided and the treatment delivery structure 96 includes an electrode 108 (FIG. 9) to engage and provide electrical stimulation to disordered tissue 102. Instead of providing electrical stimulation, the treatment delivery structure 96 can be configured to provide drugs, hormones, synthetic materials, cells, tissues/bioengineered tissues and/or chemicals to the disordered tissue 102.

For treatment by electrically stimulating tissue, a source of energy 106, preferably electrical energy is provided and the treatment delivery structure 96 includes an electrode 108 (FIG. 9) to engage and provide electrical stimulation to disordered tissue 102. Instead of providing electrical stimulation, the treatment delivery structure 96 can be configured to provide drugs, hormones, synthetic materials, cells, tissues/bioengineered tissues and/or chemicals to the disordered tissue 102.

Although electrodes have been disclosed to sense the normal tissue energy and of the change in energy due to the disordered tissue, other energy sensing devices can be employed. For example, an energy sensor structure that can detect electromagnetic energy changes in tissue can be employed.

Figure 10:
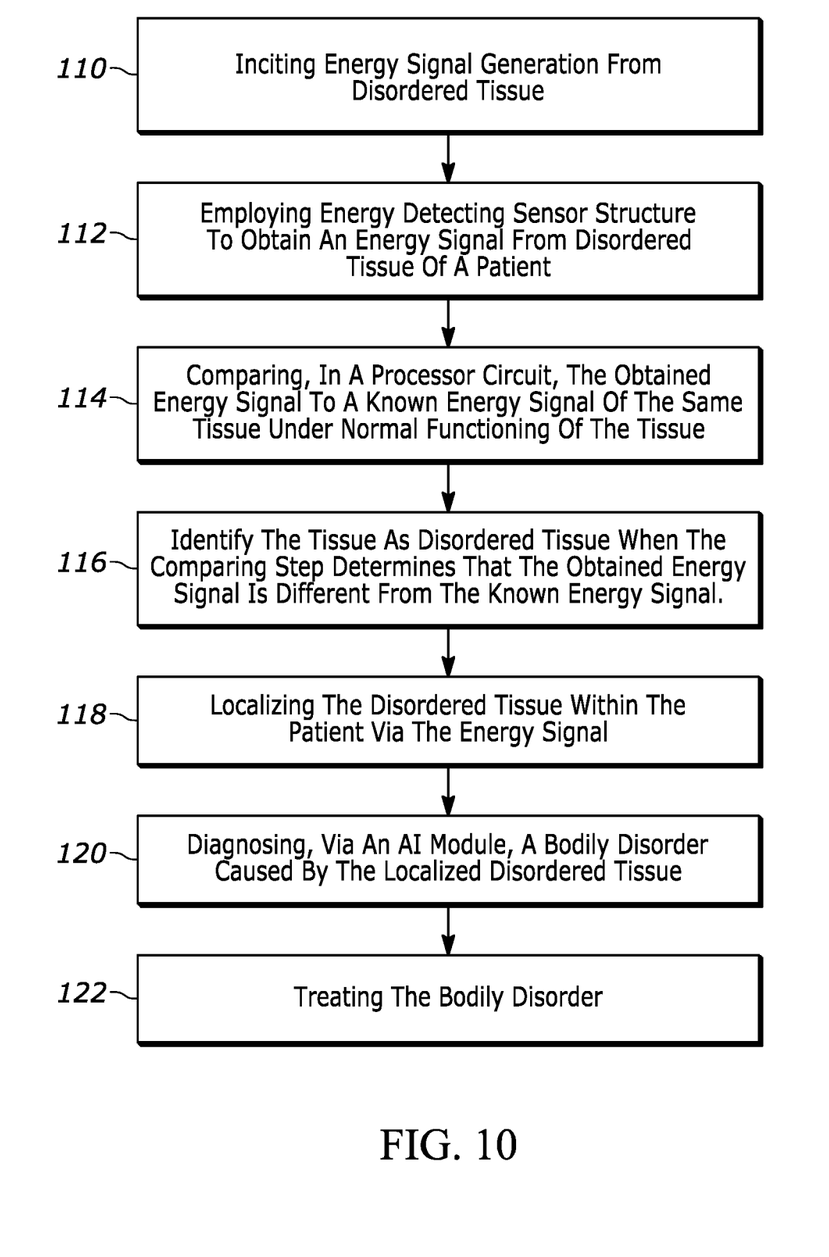
FIG. 10 is a flowchart of steps of another method of the embodiment.

With reference to FIG. 10, a method of determining and treating disordered tissue in a patient is disclosed. In step 110, energy signal generation is induced from disordered tissue (e.g., via water load). In step 112, energy detecting sensor structure (e.g., 11, 12, 12', 12''), is employed to obtain an energy signal from tissue of a patient. In step 114, the obtained energy signal is compared in a processor circuit 44 to a known energy signal of the same tissue under normal functioning of the tissue. In step 116, the tissue is identified as disordered tissue when the comparing step determines that the obtained energy signal is different from the known energy signal. In step 118, the disordered tissue is localized (e.g., via triangulation/trilateration as noted above) within the patient via the energy signal. In step 120, a bodily disorder is diagnosis (via the AI module 49) that is caused by the localized disordered tissue. In step 122, the bodily disorder is then treated.

The operations and algorithms described herein can be implemented as executable code within the microprocessor circuits 42, 44 as described, or stored on a standalone computer or machine readable non-transitory tangible storage medium that are completed based on execution of the code by a processor circuit implemented using one or more integrated circuits. Example implementations of the disclosed circuits include hardware logic that is implemented in a logic array such as a programmable logic array (PLA), a field programmable gate array (FPGA), or by mask programming of integrated circuits such as an application-specific integrated circuit (ASIC). Any of these circuits also can be implemented using a software-based executable resource that is executed by a corresponding internal processor circuit such as a micro-processor circuit and implemented using one or more integrated circuits, where execution of executable code stored in an internal memory circuit causes the integrated circuit(s) implementing the processor circuit to store application state variables in processor memory, creating an executable application resource (e.g., an application instance) that performs the operations of the circuit as described herein. Hence, use of the term "circuit" in this specification refers to both a hardware-based circuit implemented using one or more integrated circuits and that includes logic for performing the described operations, or a software-based circuit that includes a processor circuit (implemented using one or more integrated circuits), the processor circuit including a reserved portion of processor memory for storage of application state data and application variables that are modified by execution of the executable code by a processor circuit. The memory circuits 35, 51 can be implemented, for example, using a non-volatile memory such as a programmable read only memory (PROM) or an EPROM, and/or a volatile memory such as a DRAM, etc.

The foregoing preferred embodiments have been shown and described for the purposes of illustrating the structural and functional principles of the present invention, as well as illustrating the methods of employing the preferred embodiments and are subject to change without departing from such principles. Therefore, this invention includes all modifications encompassed within the spirit of the following claims.

What is claimed is:

1. A method of determining disordered tissue in a patient comprising the steps of:

inducing energy signal generation from disordered tissue,
employing energy detecting sensor structure to obtain an energy signal from tissue of a patient,
comparing, in a processor circuit, the obtained energy signal to a known energy signal of the same tissue under normal functioning of the tissue, identifying the tissue as disordered tissue when the comparing step determines that the obtained energy signal is different from the known energy signal, and diagnosing, via an Artificial Intelligence (AI) module, a bodily disorder caused by the disordered tissue, wherein the disordered tissue is associated with endometriosis, and the known energy signal is a frequency signal less than 8 cpm and the obtained energy signal is a frequency signal in the range of 12-60 cpm.

2. The method of claim 1, further comprising the step of treating the bodily disorder, wherein the treating step includes treating the disordered tissue, or tissue affected by the disordered tissue, with surgery, EMF, electric stimulation treatment, drugs, hormones, synthetic materials, cells, tissues, bioengineered tissues or chemicals.

3. The method of claim 2, wherein the energy detecting sensor structure and processor circuit are part of a wearable, single unit, the single unit further including a transmitter, the method further comprising:

transmitting instructions via the transmitter to a separate device, with the separate device performing the treating step.

4. The method of claim 2, wherein the energy detecting sensor structure and processor circuit are part of a wearable, single unit, the single unit further including a treatment delivery structure constructed and arranged to perform the treating step.

5. The method of claim 2, wherein the energy detecting sensor structure is movably housed in a tube structure and the method further includes inserting the tube structure through a bodily orifice and moving the energy sensor structure to extend from a distal end of the tube structure to an operative position to obtain the energy signal from the tissue of a patient.

6. The method of claim 5, wherein the treating step includes delivering treatment through the distal end of the tube structure while tube structure remains within the bodily orifice.

7. The method of claim 1, wherein the energy detecting sensor structure is employed externally of the body of the patient.

8. The method of claim 1, wherein the energy detecting sensor structure is employed internally of the body of the patient.

9. The method of claim 1, further comprising the step of localizing the disordered tissue within the patient via the energy signal, wherein the localizing step is performed by the AI module using triangulation and/or trilateration.

10. The method of claim 1, further comprising:

determining, via the AI module, propagation of the disordered tissue within the body.

11. The method of claim 1, wherein the employed energy detecting sensor structure comprises a plurality of electrodes.

12. The method of claim 1, wherein the inducing step includes causing the patient to consume a water load.

13. The method of claim 1, wherein the diagnosing step includes employing the Artificial Intelligence (AI) module to determine if the patients tests negative for having the bodily disorder and configured to determine a false negative.

14. The method of claim 13, further comprising a memory circuit storing data relating to specific patient information, and wherein the AI module is further configured to search the memory circuit and employ the patient information to determine a probability level of a positive diagnosis of the bodily disorder.

15. The method of claim 1, wherein the diagnosing step includes employing the Artificial Intelligence (AI) module that is connected to a network, the AI module being configured to access and analyze data collected from other patients via the network for use in making the diagnosis.

16. A method of determining disordered tissue in a patient comprising the steps of:

inducing energy signal generation from disordered tissue, employing energy detecting sensor structure to obtain an energy signal from tissue of a patient, comparing, in a processor circuit, the obtained energy signal to a known energy signal of the same tissue under normal functioning of the tissue, identifying the tissue as disordered tissue when the comparing step determines that the obtained energy signal is different from the known energy signal, and diagnosing, via an Artificial Intelligence (AI) module, a bodily disorder caused by the disordered tissue, wherein the disordered tissue is tissue causing a bowel spasm or obstruction, and the known energy signal is a frequency signal within the range of 3-15 cpm and the obtained energy signal is a frequency signal in the range of 50-70 cpm or 180-200 cpm.

17. A method of determining disordered tissue in a patient comprising the steps of:

inducing energy signal generation from disordered tissue, employing energy detecting sensor structure to obtain frequency of contraction of the bowel, and identifying the disordered tissue as endometriosis tissue when the obtained frequency of contraction of the bowel is in the range of 12-60 cpm.

18. The method of claim 17, wherein the step of inducing energy signal generation includes causing the patient to consume a water load.

19. The method of claim 17, wherein the energy detecting sensor structure includes electrodes.

20. A method of determining disordered tissue in a patient comprising the steps of:

inducing energy signal generation from disordered tissue, employing energy detecting sensor structure to obtain an energy signal from tissue of a patient, comparing, in a processor circuit, the obtained energy signal to a known energy signal of the same tissue under normal functioning of the tissue, identifying the tissue as disordered tissue when the comparing step determines that the obtained energy signal is different from the known energy signal, and diagnosing, via an Artificial Intelligence (AI) module, a bodily disorder caused by the disordered tissue, wherein the disordered tissue is associated with biliary tissue and the known energy signal is a frequency signal within the range of 1-2 cpm and the obtained energy signal is a frequency signal within the range of 12-18 cpm.

21. A method of determining disordered tissue in a patient comprising the steps of:

inducing energy signal generation from disordered tissue, employing energy detecting sensor structure to obtain frequency of contraction of the bowel, and employing an Artificial Intelligence (AI) module to identify the disordered tissue as uterine tissue when the obtained frequency of contraction of the bowel is outside the range of 1-3 cpm or, during menstruation, outside the range of 4-8 cpm.

* * * * *